(12) United States Patent
Osorio

(10) Patent No.: US 12,727,812 B2
(45) Date of Patent: Sep. 8, 2026

(54) AUTOMATED SEIZURE DETECTION, QUANTIFICATION, WARNING AND THERAPY DELIVERY USING THE SLOPE OF HEART RATE

(71) Applicant: Ivan Osorio, Reddick, FL (US)

(72) Inventor: Ivan Osorio, Reddick, FL (US)

( * ) Notice: Subject to any disclaimer, the term of this patent is extended or adjusted under 35 U.S.C. 154(b) by 0 days.

(21) Appl. No.: 18/404,863

(22) Filed: Jan. 4, 2024

(65) Prior Publication Data

US 2024/0138751 A1 May 2, 2024

Related U.S. Application Data

(63) Continuation of application No. 17/040,921, filed as application No. PCT/US2019/026389 on Apr. 8, 2019, now abandoned.

(60) Provisional application No. 62/654,168, filed on Apr. 6, 2018.

(51) Int. Cl.

| | |
|---|---|
| ***A61B 5/00*** | (2006.01) |
| ***A61B 5/0205*** | (2006.01) |
| ***A61B 5/021*** | (2006.01) |
| ***A61B 5/024*** | (2006.01) |
| ***A61B 5/026*** | (2006.01) |
| ***A61B 5/11*** | (2006.01) |
| ***A61B 5/352*** | (2021.01) |

(52) U.S. Cl.

CPC ........ *A61B 5/4094* (2013.01); *A61B 5/02055* (2013.01); *A61B 5/021* (2013.01); *A61B 5/02405* (2013.01); *A61B 5/026* (2013.01); *A61B 5/1118* (2013.01); *A61B 5/352* (2021.01); *A61B 5/746* (2013.01); *A61B 2560/0252* (2013.01)

(58) Field of Classification Search

CPC ... A61B 5/4094; A61B 5/02405; A61B 5/352; A61B 5/746

See application file for complete search history.

(56) References Cited

U.S. PATENT DOCUMENTS

2011/0270096 A1* 11/2011 Osorio ................. A61B 5/7275 600/483
2012/0271181 A1* 10/2012 Liao ..................... A61B 5/4094 600/508
2012/0310050 A1* 12/2012 Osorio ................... G16H 20/40 600/300
2014/0275838 A1* 9/2014 Osorio .................. A61B 5/1118 600/595

(Continued)

*Primary Examiner* — Amanda L Steinberg
*Assistant Examiner* — Laura Hodge
(74) *Attorney, Agent, or Firm* — Fuller IP Law LLC; Rodney J. Fuller

(57) ABSTRACT

A system and method for detecting seizures in a patient are disclosed. The method includes measuring at least one signal associated with the patient over a first time period, and calculating a first slope having a rate of change in a first signal of the at least one signal over the first time period. The first signal is a heart rate. The method also includes determining a difference between the first slope and a reference slope, as well as detecting an epileptic seizure based at least upon the difference between the first slope and the reference slope. Furthermore, the method includes quantifying the epileptic seizure by calculating a severity of the seizure. The severity is the product of a seizure duration and a seizure intensity.

20 Claims, 4 Drawing Sheets

(56) References Cited

U.S. PATENT DOCUMENTS

2017/0035368 A1* 2/2017 Osorio ............... A61N 1/36514
2017/0095194 A1* 4/2017 Krauss ................... G16H 40/67

* cited by examiner

AUTOMATED SEIZURE DETECTION, QUANTIFICATION, WARNING AND THERAPY DELIVERY USING THE SLOPE OF HEART RATE

RELATED APPLICATIONS

This application is a Continuation of U.S. patent application Ser. No. 17/040,921, filed Sep. 23, 2020, which is the U.S. National Stage of International Patent Application No. PCT/US2019/026389, filed Apr. 8, 2019, which claims the benefit of U.S. provisional patent application 62/654,168, filed Apr. 6, 2018, the contents of each of which are hereby incorporated by reference in their entireties.

TECHNICAL FIELD

Aspects of this document relate generally to seizure detection and quantification.

BACKGROUND

Identification of changes in brain state (whether physiologic or pathologic) has traditionally been accomplished through analysis of electrical brain signals and behavioral observation. Continuous (e.g., round-the-clock) automated monitoring of changes in brain state imposes certain limitations on the utilization of these traditional methods, due to the difficulties inherent to automated ambulatory video, the large amount of data produced per unit time, and the excessive demands on human and technical resources required to maintain an acceptable signal/noise for electrical signals recorded from the scalp. Additionally, scalp signals have poor temporospatial resolution, a characteristic which results in both low sensitivity and specificity of state-of-brain detection changes.

Implanted sensors or electrodes beneath the scalp but above the outer skull table or intra-cranial (epidural, subdural or depth) have been used to overcome the limitations of scalp recordings. However, although the quality of recordings (especially for intracranial electrodes) is much better (e.g., typically has a higher S/N (signal to noise ratio)) than that from scalp electrodes, the quality is still limited and there are risks (e.g., infection, bleeding, brain damage) associated with these devices, not to mention cost and scarcity of neurosurgeons to perform this type of procedures. Because of the intrusiveness of electrocorticographic ("EEG") and other sensors, it is highly desirable to detect signals using other signals that are more readily available to measure. Cardiac signals are typically relatively easy to measure and the autonomic and neurologic systems are interlinked in numerous ways.

SUMMARY

According to one aspect, the present disclosure provides a method of detecting seizures in a patient, comprising: measuring at least one signal associated with the patient over a first time period; calculating a first slope comprising a rate of change in a first signal of the at least one signal over the first time period, wherein the first signal is a heart rate; determining a difference between the first slope and a reference slope; detecting an epileptic seizure based at least upon the difference between the first slope and the reference slope; and quantifying the epileptic seizure by calculating a severity of the seizure, wherein the severity is the product of a seizure duration and a seizure intensity, the seizure duration is the amount of time the difference between the first slope and the reference slope spent outside a threshold value, and the seizure intensity is a maximum value of the first slope during the seizure.

According to some aspects, the reference slope is based upon one or more signal measurements performed under inter-ictal circumstances including at least one of physical activity, resting, high ambient temperature, daytime, and nighttime. According to certain aspects, the first time period is equivalent to three heart beats of the patient. According to some aspects, the first slope is calculated by comparing a time interval between a first R wave peak and a second R wave peak with a time interval between the second R wave peak and a third R wave peak. According to some aspects, the method further comprises warning at least one of the patient and a caregiver of the detection of an epileptic seizure. According to some aspects, the method further comprises classifying the detected epileptic seizure. According to some aspects, each signal of the at least one signal is an autonomic signal, and is one of cardiac, vascular, respiratory, and dermal.

According to one aspect, the present disclosure provides a method of detecting seizures in a patient, comprising: measuring at least one signal associated with the patient over a first time period; calculating a first slope comprising a rate of change in a first signal of the at least one signal over the first time period; determining a difference between the first slope and a reference slope; and detecting an epileptic seizure based at least upon the difference between the first slope and the reference slope.

According to some aspects, each signal of the at least one signal is an autonomic signal including one or more of the following signals: EKG, PKG, Echocardiography, Apexcardiography (ApKG), Intra-cardiac pressure, Cardiac blood flow, cardiac thermography; heart rate (HR), change of HR, rate of change of HR, heart rate variability (HRV), change of HRV, rate of change of HRV, or HRV vs. HR. According to certain aspects, the first signal is a heart rate. According to some aspects, the first time period is equivalent to three heart beats of the patient. According to various aspects, the first slope is calculated by comparing a time interval between a first R wave peak and a second R wave peak with a time interval between the second R wave peak and a third R wave peak. According to some aspects, the reference slope is based upon one or more signal measurements performed under inter-ictal circumstances including at least one of physical activity, resting, high ambient temperature, daytime, and nighttime. According to some aspects, the method further comprises warning at least one of the patient and a caregiver of the detection of an epileptic seizure. According to some aspects, the method further comprises quantifying the epileptic seizure by calculating a severity of the seizure, wherein the severity is the product of a seizure duration and a seizure intensity, the seizure duration is the amount of time the difference between the first slope and the reference slope spent outside a threshold value, and the seizure intensity is a maximum value of the first slope during the seizure. According to some aspects, the method further comprises classifying the detected epileptic seizure in response to determining that at least one of the intensity and the duration are above the 75th percentile or below the 25th percentile of values for representative seizures.

According to one aspect, the present disclosure provides a medical device system for detecting seizures in a patient, comprising: a cardiac sensor configured to measure a heart rate of the patient over at least a first time period; a controller configured to calculate a first slope comprising a rate of change in the heart rate over the first time period, the controller determining a difference between the first slope and a reference slope, and the controller detecting an epileptic seizure based at least upon the difference between the first slope and the reference slope.

According to some aspects, the first time period is equivalent to three heart beats of the patient. According to various aspects, the first slope is calculated by comparing a time interval between a first R wave peak and a second R wave peak with a time interval between the second R wave peak and a third R wave peak. According to some aspects, the reference slope is based upon one or more signal measurements performed under inter-ictal circumstances including at least one of physical activity, resting, high ambient temperature, daytime, and nighttime.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The disclosure will hereinafter be described in conjunction with the appended drawings, where like designations denote like elements, and.

DETAILED DESCRIPTION

Figure 1:
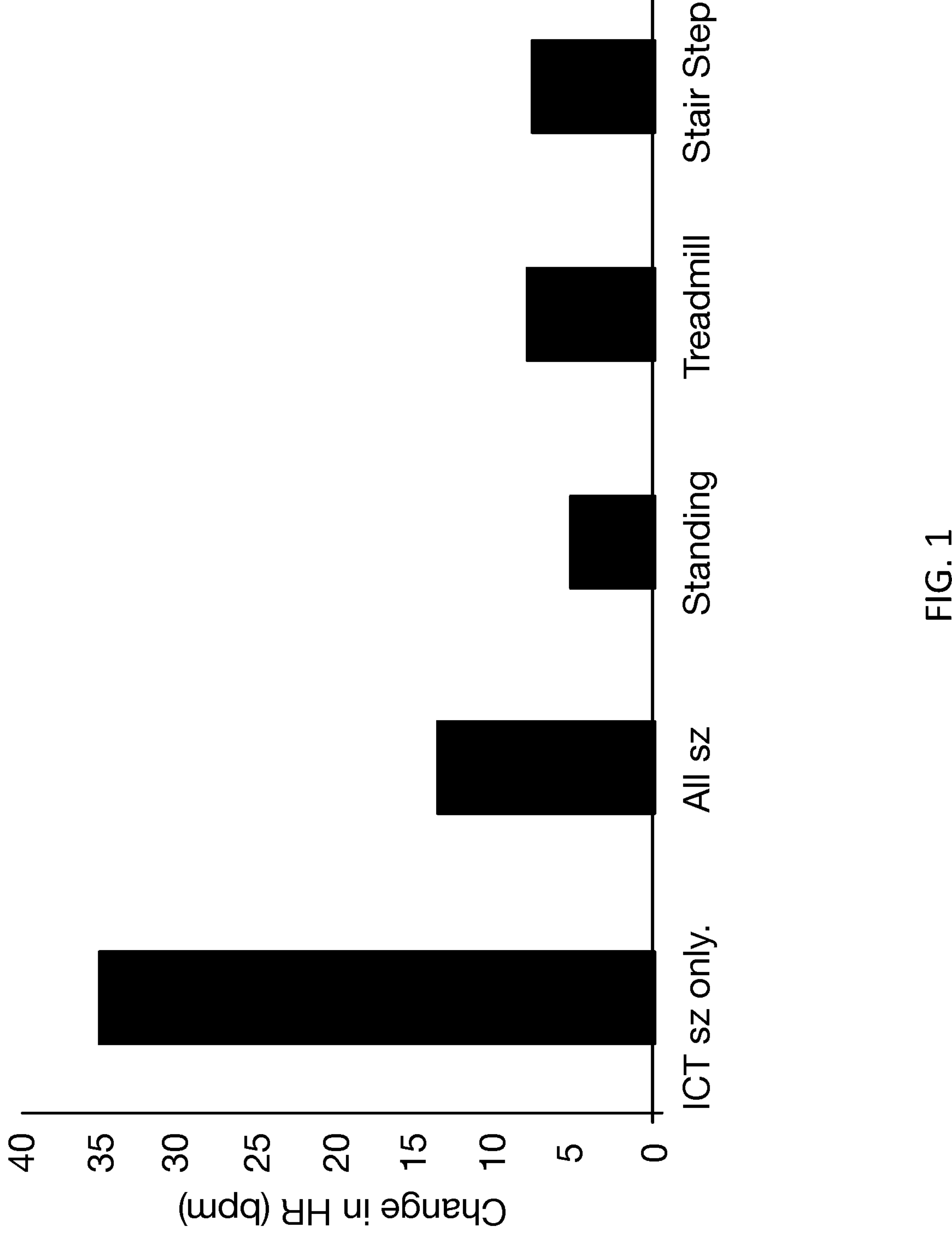
FIG. 1 is a graph of changes in heart rate associated with various physiologic activities and seizures.

This disclosure, its aspects and implementations, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes a number of embodiments in many different forms, there is shown in the drawings and will herein be described in detail particular embodiments with the understanding that the present disclosure is to be considered as an exemplification of the principles of the disclosed methods and systems, and is not intended to limit the broad aspect of the disclosed concepts to the embodiments illustrated.

The term "electrode" or "electrodes" described herein may refer to one or more stimulation electrodes (i.e., electrodes for delivering a therapeutic signal generated by an implanted medical device ("IMD") to a tissue), sensing electrodes (i.e., electrodes for sensing a physiological indication of a state of a patient's body), and/or electrodes that are capable of delivering a therapeutic signal, as well as performing a sensing function.

While electrical brain signals and behavioral observation may provide information for classification of brain states, this task can be accomplished more efficiently, more precisely, and/or more cost-effectively through monitoring of other biological signals such those generated by the heart, muscle, skin, eyes, tympanic membrane temperature, and body posture/movement, since they may not require surgery, or if surgery is required for implantation, the procedures are much shorter, simpler, and cheaper than those required for recording of brain signals.

Certain highly valuable neurologic, autonomic, endocrine, dermal, or metabolic signals may be measured on a patient for detection, quantification, and classification of state changes. A state change of particular interest is when a patient has a seizure (e.g., epileptic or non-epileptic seizures). Neurologic signals (e.g., electroencephalographic or "EEG," electrocorticographic or "ECoG," deep brain EEG, subdural EEG, intracranial EEG, etc.) can be very helpful in detecting and characterizing seizures, but many neurologic signals require intrusive sensors that complicate the desirability of ambulatory neurologic sensors. These signals can be used individually or in combination to continuously monitor the brain and generate a state-of-the-system/organ report, in real-time, for the detection, quantification, classification, validation, control and logging of physiologic or pathologic state changes. This approach takes advantage of the inherent and finely tuned dynamical coupling among these systems. For instance, changes in brain state/activity may result in changes in heart activity, muscle activity, and skin properties.

Attempts have been made to detect changes in brain state by measuring cardiac signals. Although cardiac signals are easier to observe than electrical brain signals, they are limited in their effectiveness. The performance (in terms of false positives and false negatives) of automated seizure detection using cardiac signals, and the speed with which detections are performed (measured as the difference between time of electrographic onset using intracranial electrodes vs. time of cardiac onset with chest electrodes), is predominantly (if not solely) a function of the prevalent heart rate (HR) prior to seizure onset. The higher the inter-ictal HR before a seizure, the longer the time to detection and the higher the probability of automated detection errors. In the case of seizures manifesting with tachycardia, these problems extend even to lower inter-ictal HR.

For example, parameters that consistently and accurately result in automated detections issued when the HR reaches 85 bpm for a subject in the resting state (e.g. HR 70 bpm), a 20% increase, may be less effective when applied to the same subject while physically active with a prevalent inter-ictal HR of 85 bpm or higher at time of seizure onset. If the detection parameters used for the resting state are applied while this subject is physically active, a false positive ("FP") detection will be issued when the HR is 85 bpm. Unless all physical activity ceases immediately upon issuance of the FP detection the subject may be declared in status epilepticus, as the HR will remain elevated for the duration of the physical activity and for some time thereafter.

On the other hand, if an attempt is made to avoid this potentially serious situation by either: a) raising the detection threshold (e.g. above 20% increases in the HR that yields excellent results when the subject is resting), or b) a delay is programmed so that the detection is issued seconds after the HR has increased by >20%, then the detection, warning and treatment will be delayed. A delay in one or more of seizure detection, warning or treatment can potentially lead to results including the seizure not being blocked and/or increased exposure to risks of injury or undesirable neurological or cardio-vascular outcomes.

This example not only exposes the limitations of non-adaptive (in real-time) rule-based changes in seizure detection parameters, but more relevantly, exposes the limitations inherent to detection algorithms relying solely on changes in HR that are most prominent (e.g., higher rates of FP or false negative (FN) or clinically significant delays in detection) at lower or higher inter-ictal HRs.

Contemplated herein are methods, systems, and devices that: a) detect pre-specified changes in brain state; b) quantify their duration, intensity, and time of occurrence; c) classify their type (e.g., epileptic vs. non-epileptic seizures; primarily vs. secondarily generalized seizures; generalized vs. partial seizures; complex vs., simple partial seizures; d) be used as a basis for warning and control/therapy, and e) preserve this information for future retrieval for optimization of detection, quantification and classification of state changes and assessment and optimization of therapeutic (e.g., control) efficacy. In some embodiments, detection may occur in real-time. Non-epileptic movements in this disclosure refer to those resembling movements seen during tonic-clonic seizures but which are not caused by those seizures.

In some embodiments, this may be accomplished using a single signal, such as the rate of change in heart rate. In other embodiments, the detection of seizures may include both autonomic signals (e.g., heart rate, R to R intervals, other cardiac signals, etc.) in combination with signals or markers from one or more of the following: autonomic, neurologic, endocrine, metabolic, gastro-intestinal, dermal, or tissue/organ stress. This multimodal detection using various signals of state changes takes advantage of the fact that certain brain structures directly or indirectly influence autonomic, endocrine, gastro-intestinal, dermal and metabolic functions and that certain abnormal states (e.g. seizures) stress the body tissues and result in the elevation of certain compounds or molecules (e.g., stress markers) that may be used to detect and verify the occurrence of said abnormal state. Herein, "multimodal" refers to epileptic event detection based on more than one endogenous mode or type of signal.

It has been established that seizures in humans originating from or spreading to central autonomic structures induce changes in heart rate, among other cardio-vascular indices. It should be stated that seizure-induced heart rate increases (which are far more frequent than heart rate decreases) are not primarily the result of increased motor activity or of metabolic changes, but are instead a neurogenic phenomenon. In the present disclosure, a highly robust, efficient and reliable system is provided for detecting, quantifying and/or classifying epileptic seizures based upon the rate of change in heart rate, as well as on multimodal signals and, if desired, using this information to provide warnings, therapies and optimization of all of these tasks. Systems of the present disclosure are suitable for commercial, long-term implants or external devices and provide reliable and accurate indications of seizure events for a wide variety of epilepsy patients Multimodal epileptic event detection may make use of signals or markers of autonomic, neurologic, endocrine, metabolic, gastro-intestinal, and/or dermal origin and of tissue/organ stress. Autonomic signals include cardiac, vascular, respiratory and dermal signals, which include at least the following:

Cardiac: EKG, PKG, Echocardiography, Apexcardiography (ApKG), Intra-cardiac pressure, Cardiac blood flow, cardiac thermography; from which can be derived, e.g., heart rate (HR), change of HR, rate of change of HR, heart rate variability (HRV), change of HRV, rate of change of HRV, HRV vs. HR. Also, blood pressure, heart sounds, heart rhythm, heartbeat wave morphology, heartbeat complex morphology, and thoracic wall deflection.

Vascular: Arterial Pressure, Arterial and venous blood wave pressure morphology; Arterial and venous blood flow velocity, arterial and venous blood flow sounds, arterial and venous thermography.

Respiratory: Frequency, tidal volume, minute volume, respiratory wave morphology, respiratory sounds, end-tidal $CO_2$, Intercostal EMG, Diaphragmatic EMG, chest wall and abdominal wall motion, from which can be derived, e.g., respiration rate (RR), change of RR, rate of change of RR. Also, arterial gas concentrations, including oxygen saturation, as well as blood pH can be considered respiratory signals.

Dermal: Skin resistance, skin temperature, skin blood flow, sweat gland activity Concentrations of catecholamines (and their metabolites) and acetylcholine or acetylcholinesterase activity in blood, saliva and other body fluids concentrations and its rate of change.

Neurologic signals include cognitive and behavioral signals, kinetic signals, vocalization signals, EEG and/or ECoG signals, endocrine signals, stress marker signals, and metabolic signals, which include at least the following:

Cognitive/behavioral: Level of consciousness, attention, reaction time, memory, visuo-spatial, language, reasoning, judgment, mathematical calculations, auditory and/or visual discrimination.

Kinetic: Direction, speed/acceleration, trajectory (1D to 3D), pattern, and quality of movements, force of contraction, body posture, body orientation/position, body part orientation/position in reference to each other and to imaginary axes, muscle tone, agonist- to-antagonist muscle tone relation, from which can be derived, e.g., information about gait, posture, accessory movements, falls.

Vocalizations: Formed and unformed vocalizations.

Brain Electrical Signals: EEG/ECoG, Evoked potentials, field potentials, and single unit activity.

Endocrine: Prolactin, luteinizing hormone, follicle stimulation hormone, growth hormone, ACTH, cortisol, vasopressin, beta-endorphin, beta, lipotropin.-, corticotropin-releasing factor (CRF).

Stress Markers: Reactive oxygen and nitrogen species including but not limited to iso- and neuro-prostanes and nitrite/nitrate ratio, gluthatione, gluthatione disulfide and gluthatione peroxidase activity, citrulline, protein carbonyls, thiobarbituric acid, the heat shock protein family, catecholamines, lactic acid, N-acetylaspartate, and metabolites of any of the foregoing.

Metabolic: arterial pH and gases, lactate/pyruvate ratio, electrolytes, and glucose.

Brain activity (e.g., electrical, cognitive, affective), whether normal or abnormal (e.g., seizures), may affect the function of the autonomic nervous system. Moreover, given the close interaction between the autonomic nervous system and organs to which it is coupled (e.g., heart, lungs, pupils), these organs may also be profoundly affected by brain activity. Examples of the effects of brain activity include changes in respiratory rates and heart rhythms. More specifically, one striking example of the interaction between brain state and the cardio-respiratory system is the observation that anesthetized humans breathing spontaneously, stopped breathing at reduced arterial concentrations of $CO_2$ that did not impair/alter their breathing while awake. This phenomenon known as the "wakefulness effect" underscores: a) the vital importance of the activating role on cardio-respiratory functions of increased neural influences present during wakefulness compared to depressed levels of consciousness, as seen for example during certain seizures or immediately after their termination; placed in a clinical/practical context, a reticulo-thalamo-cortical system that is either activated or can be activated, is a safeguard against extreme or catastrophic events of a cardio-respiratory nature; b) the greater susceptibility to respiratory and cardiac dysfunction in subjects with depressed levels of consciousness whether physiologic (e.g., sleep) or pathologic (ictal or post-ictal states); said dysfunction is not limited to changes in rate or tidal volume (e.g. hypopnea, apnea or hypoventilation) but encompass rhythm (cardiac or respiratory arrhythmias), pattern (e.g. Cheyne-Stokes breathing; agonal breathing) or morphology of either EKG complexes (e.g. PVC's, S-T segment elevation) or breaths (e.g., apneustic breathing); c) the critical importance for sensitivity, specificity and speed of detection and quantification/estimation of increased risk of death in epilepsy patients, to include tests of arousability or responsiveness in the assessment and decision, since loss of consciousness occurs within seconds of severe hypoxemia or ischemia associated with life-threatening cardio-respiratory dysfunction; it thus follows that if a patient is arousable and/or more particularly if the cognitive performance is intact the probability that the change in cardio-respiratory function is life threatening is small, if not negligible; d) the therapeutic value of delivering stimuli that cause arousal to decrease the risk of death in certain situations.

Of the various signals mentioned above, heart rate is among the easiest to automatically monitor using inexpensive devices. However, as discussed above, there are severe limitations in using heart rate to detect changes in brain state. Contemplated herein are methods, systems, and devices that make use of the slope, or rate of change, in heart rate for automated seizure detection, quantification, warning and therapy delivery. As will be discussed in greater detail below, examination of the rate of change in heart rate, rather than the heart rate itself, overcomes the limitations of conventional heart rate-based methodologies. In some embodiments, the slope of the heart rate alone is used, while in others, the slope of the heart rate is used in conjunction with one or more of the signals discussed above (i.e. multimodal embodiments).

This system and method is advantageous over existing methods at least because it does not require bi-variate (e.g., HR and kinetic activity) or multi-variate (e.g., HR, kinetic activity and electrodermal signals) signals to achieve performance comparable to existing methods (e.g., speed of detection and rates of false positives and false negatives) applied to subject with epilepsy in a resting state. However, the use of multimodal signals may provide additional accuracy, as will be discussed below.

The use of the slope of the heart rate allows for implementation within a simpler architecture, having lower computational demands and higher speed of detection. For example, in some embodiments, detection may occur as early as the time it takes to record, process and analyze two heart beats.

Heart rate is modulated or adjusted by both neurogenic and metabolic activity. Neurogenic modulation may be physiologic (e.g., exercise) or paroxysmal/pathological (e.g., seizures). The rate of change in HR depends on the type of impulses generated from brain structures such as the central autonomic network. Paroxysmal modulation causes a faster change in HR than physiologic activity such as exercise, which is largely independent of the prevalent inter-ictal HR.

See, for example, FIG. 1, which compares the rate of change in HR associated with various physiologic activities and seizures. The activities and seizures shown include "ICT sz only" (i.e. seizures with tachycardia), "All sz" (i.e. seizures with and without ictal tachycardia), "Standing" (i.e. standing up from a recumbent position), "Treadmill" (i.e. walking and jogging on treadmill), and "Stair Step" (i.e. climbing up and down stairs). The rate of change in HR of seizures was 5-7 times greater than the rate of change of HR due to different physical activities. These observations were made on a sample of data from a study that investigated the differences in HR changes between physical activity/exercise.

Figure 2:
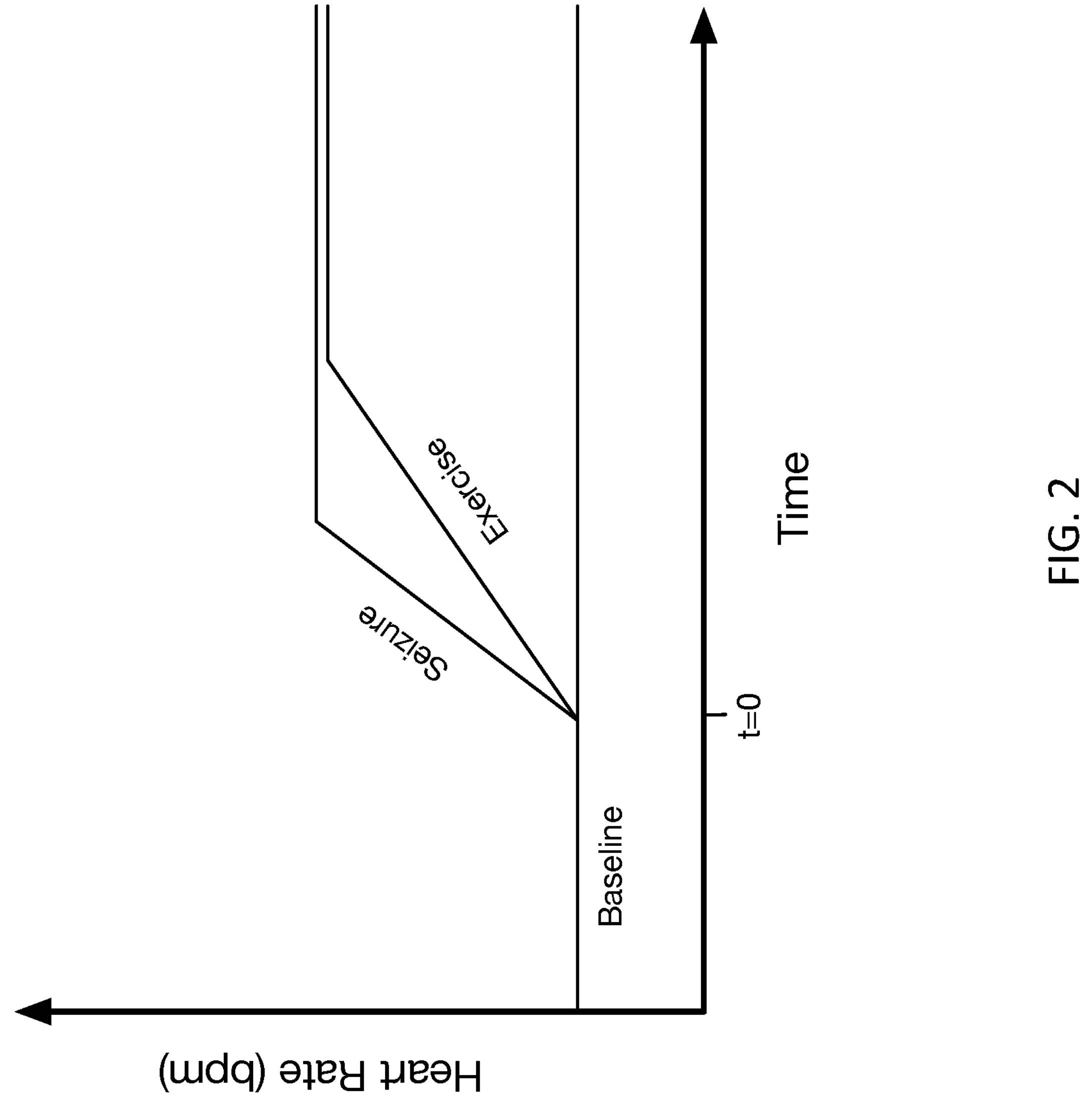
FIG. 2 is a graph of the time evolution of physiological and ictal increases in heart rate.

It should be noted that the actual heart rates (as opposed to their rate of change) for these various activities and seizures may be quite similar, making accurate detection based on HR alone difficult. This is illustrated in FIG. 2. FIG. 2 is an idealized plot of the representative time evolution of a subjects heart rate under three difference scenarios: baseline (i.e. resting state), exercise (i.e. physically active state), and seizure (i.e. ictal state). The exercise and seizure states begin at time t=0, after which the heart rate begins to rise. As shown, the slopes of the heart rate (e.g. the rate of change in the heart rate) for the exercise and seizure scenarios differ, even though the magnitude of physiological and ictal increases in HR in a given subject may be similar or identical. The seizure slopes are largely independent of prevalent inter-ictal HR.

Figures 3A, 3B:
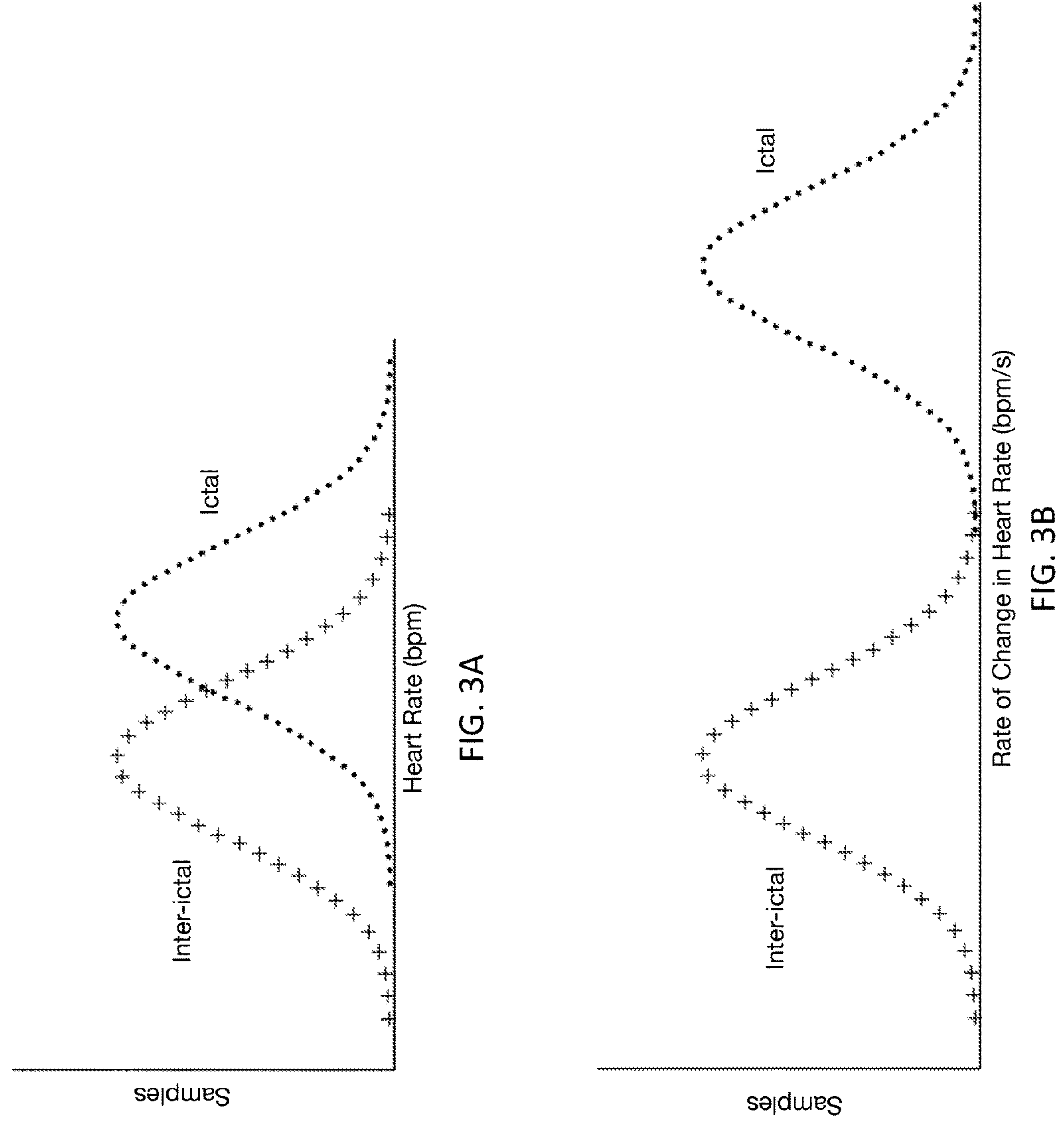
FIGS. 3A and 3B are distributions of heart rates and rates of change in heart rates, respectively, associated with inter-ictal and ictal states.

FIGS. 3A and 3B are histograms showing the distribution of heart rates (FIG. 3A) and rates of change of HR (FIG. 3B) for inter-ictal ("+") and ictal ("•") states. As shown in FIG. 3A, the heart rate distributions for ictal and inter-ictal states have a non-negligible degree of overlap that decreases the ability to accurately and rapidly detect seizures. When the slope, or rate of change, of HR is used as the detection variable, these distributions separate, as shown in FIG. 3B, providing for more accurate and earlier detections.

The difference in the rate of change of heart activity between exercise and seizures may be measured as differences in the steepness of the seizure slope ($\Delta HRsz/\Delta Tsz$) and the exercise slope ($\Delta HRe/\Delta Te$) or some other reference value (resting awake $\Delta HRrw/\Delta Trw$; asleep $\Delta HRs/\Delta Ts$; etc.) within a time period.

In some embodiments, the rate of HR change, or the slope of the HR when plotted against time, may be estimated as the slope of the secant line defined by two HR measurements. The accuracy and responsiveness of such a method may be limited to the measurement frequency of the HR monitoring device.

In other embodiments, the rate of HR change may be also estimated in windows containing at least 3 heart beats (e.g., R wave peaks), by measuring the R-R intervals' duration and determining any changes in this value [(R1-R2)-(R2-R3)]. Changes in R-R interval durations that are different (e.g., shorter) from a relevant/applicable reference value, indicate a change in the slope. For example, decreasing intervals indicate an increasing HR slope.

In still other embodiments, the HR slope may be defined as the change in HR over the time it takes for the HR to reach its zenith (i.e. global maxima). While this method may reduce the number of false positives, it is inherently slower than R-R interval measurements. Those skilled in the art will recognize that a rate of change in a measured signal may be determined using a variety of other methods which may be implemented in various embodiments of the methods, systems, and devices contemplated herein.

Measures of central tendency (e.g., median) may be applied to the data collected during ictal and non-ictal states; the non-ictal state recordings may be undertaken under various conditions (e.g., physical activity, resting, high ambient temperature, day vs. night, etc.) to derive reference values that may be used for automated detection & quantification purposes. In many cases, measured values below or above those observed during non-ictal conditions (subject resting or physically active) would be indicative of seizures.

According to various embodiments, upon determination of the inception of a seizure, a warning may be issued to the subject and/or to a caregiver. In some embodiments, the warning may be accompanied by some form of treatment or therapy previously determined to be compatible with the detected state and that particular subject.

Seizure metrics may be derived from at least one of intensity, duration spread or an inter-seizure interval (defined as the time (in seconds or minutes) elapsed between the onset of consecutive seizures; (See Osorio et al., Epilepsia 1998; 2002; EJN, 2009; PRE 2010), or from two or more in any possible combination. For example, a) a seizure severity index may be the average of the percentiles of intensity, duration and extent of spread; b) peak seizure energy may be the product of peak intensity and duration; c) the sum of seizure severity (as defined immediately above) measured at each body organ where the seizure exerts its action, divided by the total number of body organs, or more restrictively, the measurement may be limited to one organ such as brain where its severity is the sum at each brain site engaged in seizure activity; d) As the time spent in seizure over a certain time window; e) as the product of the sum of seizure severities and time spent in seizure over a certain time window. Those of ordinary skill in the art appreciate that seizure metrics may be derived using other mathematical approached. Values of seizure metrics indicative of an extreme seizure may be more than two standard deviations above the mean for seizure energy or severity and below the mean for inter-seizure intervals with respect to normal or normalized distribution. Additionally, because a seizure may impact (mildly or severely, reversibly or irreversibly) body organs/systems, indices may be estimated or measured for each of the following: autonomic, neurologic, tissue stress, endocrine, metabolic and/or physical fitness/integrity. For example, generalized tonic-clonic seizures (i.e., convulsion) cause transient hypoxemia, hypercarbia, tachycardia, lactic acidosis and increases in CK, among others.

Those skilled in the art know that non-Gaussian distributions may be normalized by, for example, applying to the data logarithmic transformations so that mean, standard deviation and other measures may be estimated. The approach of treating certain seizures as extreme events lends itself to a statistical or probabilistic approach for the prevention of status epilepticus through their anticipation or early detection. The following "metrics" alone or in any combination will be used to classify a seizure or seizures into extreme as compared to non-extreme by quantifying one or more of the following:

1. Magnitude and rate of increase in seizure energy or intensity, seizure duration or extent of seizure spread (note that one type of seizure severity index may be derived from the values of at least two of these three metrics), magnitude, rate of change (e.g., drop from seizure to the post-ictal state), and/or duration in brain energy during the post-ictal state compared to a representative sample of the inter-ictal state for the patient including time of day and state (e.g., wakefulness versus sleep) and/or the rate of energy recovery from the post-ictal to the inter-ictal state; 2. Inter-seizure interval duration including the conditional probability of time to the next seizure given the time elapsed since the last seizure; 3. Seizure frequency per unit time, cumulative intensity, duration, extent, spread and/or seizure severity index (SSI) per unit time; 4. Cumulative magnitude, duration and rate of the change in post-ictal energy per unit time compared to a representative sample of the inter-ictal state for the patient including time of day and state (e.g., wakefulness versus sleep), and/or extent of spread of changes in post-ictal energy compared to a representative sample of the inter-ictal state for the patient including time of day and state (e.g., wakefulness versus sleep), 5. Magnitude and/or duration and rate of change in level of consciousness as measured using available coma scales such the Glasgow scale or qualitative classification (e.g., deep coma, superficial coma, stupor, lethargy, awake but confused) as used in clinical neurology, compared to a baseline consciousness level; 6. Magnitude, duration (when applicable, e.g., when the patient is awake) and/or rate of changes in one or more cognitive functions as measured, for example, using a reaction time or any other validated neuropsychologic test; 7. Magnitude, duration and/or rate of changes in autonomic indices such as heart rate, heart rate variability, heart rhythm, EKG, blood pressure, respirations, catecholamines, temperature and/or galvanic skin resistance, among others; 6. Magnitude, duration and/or rate of changes in metabolic indices such as arterial pH, $SaO_2$, $CO_2$, glucose and/or electrolytes, a bicarbonate (alkali acts like a pH buffer) among others; 7. Magnitude, duration and/or rates of change in endocrine indices such prolactin, cortisol, and/or growth hormone among others; and 8. Tissue stress markers such as Reactive oxygen and nitrogen species including but not limited to iso- and neuroprostanes and nitrite/nitrate ratio, gluthatione, gluthatione disulfide and gluthatione peroxidase activity, citrulline, protein carbonyls, thiobarbituric acid, the heat shock protein family, catecholamines, lactic acid, N-acetylaspartate, and metabolites of any of the foregoing tissue stress markers, free radicals, lactic acid, creatine kinase (CK), Aldolase, troponin, and/or the like.

With respect to embodiments where detection is based solely on observation of the rate of change in HR, seizure duration is computed based on the time the slope remains outside inter-ictal values during sedentary or physically active states. Seizure intensity is defined as the maximal steepness of the slope. The product of these two observables yields severity, according to various embodiments. Furthermore, in some multimodal embodiments including the slope of HR, these definitions may be used.

Changes in certain indices or features indicative of the status of autonomic, neurologic, metabolic, endocrine function and of tissue stress markers, whose magnitude, rate or duration are for example two or more standard deviation above or below a measure of central tendency (e.g., mean) for certain a duration and above the 75th percentile or below the 25th percentile of values for a certain duration may be considered as indicative of seizures, other changes of brain state. Other values for standard deviation and percentiles may be chosen to improve the predictive value. The increased risk will trigger responsive actions including but not limited to warning the subject or caregivers, providing specific care (i.e., care targeted at a seizure event itself such as electrical stimulation, seizure drug treatments, and the like; cardiac defibrillation or pacing) and/or supportive care (i.e., care targeted at other patient needs such as mechanically assisting breathing (oxygen), cooling the body and/or the brain of the patient, non-seizure medications and/or drugs, fluid intake, intubation, and/or the like), and logging the type (e.g., marked bradycardia; ventricular tachycardia; cardiac ischemia; intermittent apneas with oxygen desaturation and hypercarbia; uncompensated metabolic acidosis, etc.), time of occurrence, duration, intensity/magnitude of events and their frequency/unit time, as compared to a reference value.

The following "metrics" alone or in any combination may be used to detect seizures or to estimate or characterize other brain state changes of a patient, and may include the use of on-line and/or off-line implantable or non-implantable medical devices, continuously or intermittently. The "metrics" include, but are not limited to, magnitude, direction (e.g., increases or decrease), rate and type of change in:

Heart rate; heart rhythm/pattern; EKG morphology; cardiac size and ventricular wall size; cardiac motility and ejection fraction; blood pressure; cardiac tissue stress markers such as CK or troponin; respiratory rate and pattern; tidal volume; end-tidal $CO_2$; arterial oxygen saturation; respiratory sounds; seizure energy and/or intensity, seizure duration, and/or extent of seizure spread (note that a seizure severity index may be derived from the values of at least two of these metrics); energy during the post-ictal state compared to a representative sample of the inter-ictal state for the patient including time of day and state (e.g., wakefulness versus sleep); inter-seizure interval duration including the conditional probability of time to the next seizure given the time elapsed since the last seizure; seizure frequency per unit time; cumulative intensity, duration, extent or spread or seizure severity index/unit time; duration of the change in post-ictal energy compared to a representative sample of the inter-ictal state for the patient including time of day and state (e.g., wakefulness versus sleep); extent of spread of changes in post-ictal energy compared to a representative sample of the inter-ictal state for the patient including time of day and state (e.g., wakefulness versus sleep); cumulative change in post-ictal energy compared to a representative sample of the inter-ictal state for the patient including time of day and state (e.g., wakefulness versus sleep); magnitude and duration of change in level of consciousness as measured using available coma scales such the Glasgow scale or qualitative classification (deep coma, superficial coma, stupor, lethargy, awake but confused) as may be used in clinical neurology; magnitude and duration (when applicable; e.g., patient awake) of changes in cognitive functions as measured for example using a reaction time or any other validated neuropsychologic test; arterial pH; lactate concentration; lactate/pyruvate; glucose; electrolytes; cortisol; catecholamines and/or their metabolites in body fluids; body temperature; and/or skin resistivity.

Measures such as a Q-T variability index (QTvi), where QTvi=log 10[(QTc/QTm2)/(RRv/RRm2)]), the ratio of approximate entropy of a Q-T interval, an approximate entropy of an R-R interval (ApEnQT/ApEnRR) and/or the root mean square of successive differences between R-R interval may be also used to assess sympathetic function, risk of death and/or risk of SUDEP (Sudden Unexpected Death in Epilepsy). QTvi is a measure of cardiac repolarization lability and may provide information about the phase in which the heart is most susceptible to cardiac arrhythmias. Abnormal QTv may be associated with ventricular arrhythmias as well as sudden cardiac death, and may provide useful information in patients with epilepsy.

As mentioned above, while some embodiments may rely entirely on the determination and monitoring of the rate of change in HR, other embodiments may be multimodal, and may examine the combination of the HR slope with other signals such as blood pressure, respirations, skin resistance, or any other signal mentioned above.

In some multimodal embodiments, a cluster analysis may be implemented. A centroid may be defined in n-dimensional state space, where one dimension is the rate of HR change, and the other n-1 dimensions are any of the signals previously mentioned. The centroid may be defined using values representative of an inter-ictal or non-ictal state. Subsequent observations would be plotted in the state-space, and their distance from the centroid determined. According to various embodiments, a threshold distance from the centroid may be deemed indicative of an ictal state; observations beyond this distance from the centroid would be treated similar to the observation of an HR slope that exceeded a reference value in other, single signal embodiments.

Figure 4:
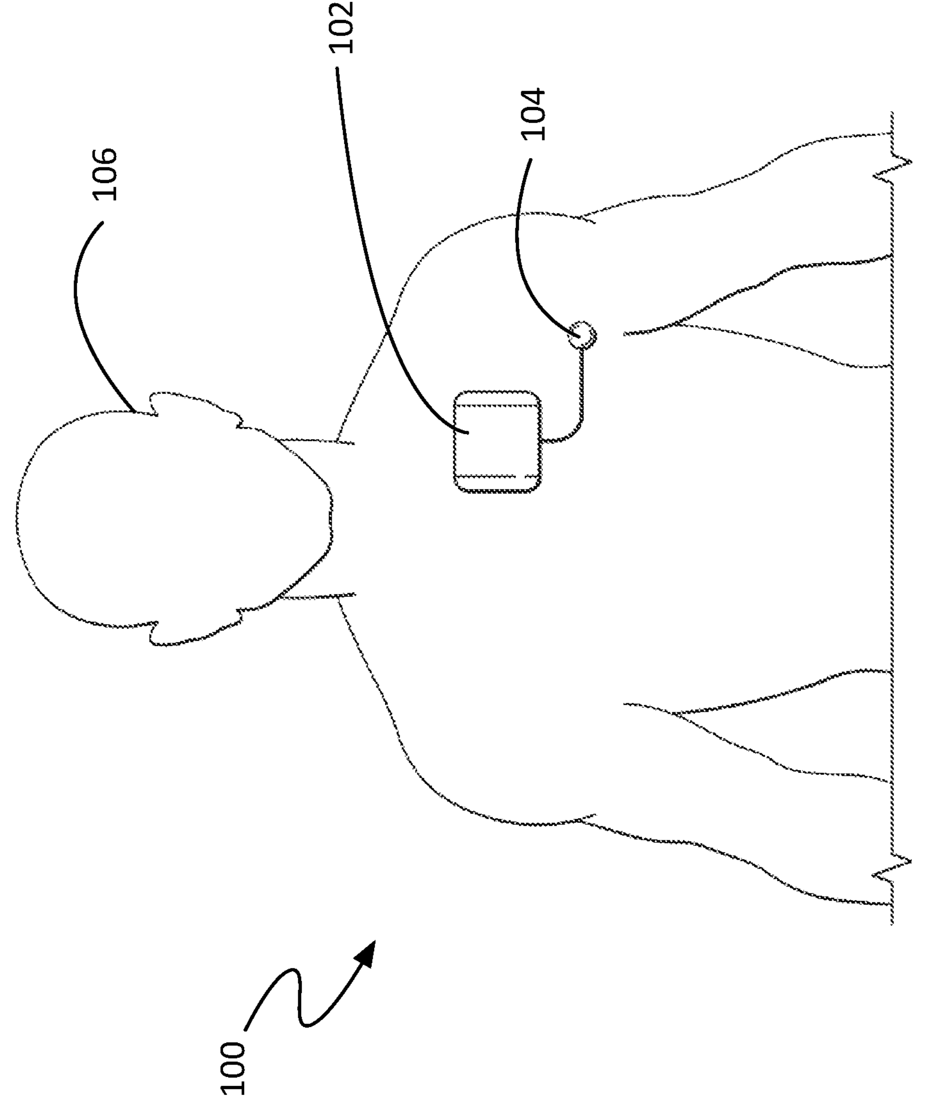
FIG. 4 is a stylized depiction of a medical device configured to detect seizures based upon the slope of a patient's heart rate.

FIG. 4 is a stylized depiction of a non-limiting example of a medical device system 100 configured to detect seizures based upon the slope of a patient's heart rate. As shown, the device comprises a controller 102 and at least one cardiac sensor 104, which is coupled to a patient 106. Other embodiments may comprise additional sensors to monitor multimodal signals, as discussed above. In some embodiments, the device 100 may be compact and portable, allowing a patient 106 to monitor their status while mobile and away from bulky conventional equipment. In certain embodiments, medical device system is implanted in the body of the patient. In some embodiments, the sensor or sensors may be wired to the controller 102, while in other embodiments the sensors may make use of wireless communications. In one embodiment, the controller 102 may be coupled to a wearable computing device, such as a smart watch, to obtain heart rate data. In another embodiment, the entire system 100 may be implemented within a smart watch.

Where the above examples, embodiments and implementations reference examples, it should be understood by those of ordinary skill in the art that other heart rate measurement and biological signal measurement methods, devices and examples could be intermixed or substituted with those provided. In places where the description above refers to particular embodiments of automated seizure detection, quantification, warning and therapy delivery systems, devices, and methods, it should be readily apparent that a number of modifications may be made without departing from the spirit thereof and that these embodiments and implementations may be applied to other to detection technologies as well. Accordingly, the disclosed subject matter is intended to embrace all such alterations, modifications and variations that fall within the spirit and scope of the disclosure and the knowledge of one of ordinary skill in the art.

What is claimed is:

1. A medical device for detecting seizures in a patient, comprising:

a cardiac sensor configured to measure a heart rate of the patient over at least a first time period equivalent to three heart beats of the patient;

a controller communicatively coupled to the cardiac sensor and configured to:

receive the heart rate from the cardiac sensor;

calculate a first slope, the first slope being at least an estimate of a rate of change in the heart rate over the first time period;

determine a difference between the first slope and a reference slope, the reference slope being a reference value for changes in R-R interval durations during non-ictal conditions;

detect an epileptic seizure based upon the difference between the first slope and the reference slope; and automatically deliver a warning and a treatment to the patient in response to the detection of an epileptic seizure, the treatment being one of an electrical stimulation and a seizure drug treatment;

wherein the first slope is calculated by comparing a time interval between a first R wave peak and a second R wave peak with a time interval between the second R wave peak and a third R wave peak.

2. The medical device of claim 1, wherein the reference slope is based upon one or more heart rate measurements performed under inter-ictal circumstances including at least one of physical activity, resting, ambient temperature, daytime, and nighttime.

3. The medical device of claim 1, wherein the controller is further configured to receive at least one autonomic signal in addition to the heart rate and to utilize the at least one autonomic signal, along with the first slope, in detecting the epileptic seizure, wherein each autonomic signal of the at least one autonomic signal is one of cardiac, vascular, respiratory, and dermal.

4. The medical device of claim 3, wherein the epileptic seizure is detected based upon a cluster analysis performed by the controller in a state space having a dimension for each autonomic signal of the at least one autonomic signal and a dimension for the first slope, wherein the cluster analysis employs a centroid defined, at least in part, using the reference slope.

5. The medical device of claim 1, wherein the detection of the epileptic seizure occurs in real-time.

6. The medical device of claim 1, wherein the controller is further configured to:

calculate a seizure duration and a seizure intensity, and then quantify the epileptic seizure by calculating a severity of the epileptic seizure;

wherein the severity is a product of the seizure duration and the seizure intensity;

wherein the seizure duration is an amount of time the difference between the first slope and the reference slope spent outside a threshold value; and wherein the seizure intensity is a maximum value of the first slope during the epileptic seizure.

7. The medical device of claim 6, wherein the controller is further configured to classify the detected epileptic seizure in response to determining that at least one of the seizure intensity and the seizure duration are above a 75th percentile or below a 25th percentile of values for representative seizures.

8. The medical device of claim 1, wherein the cardiac sensor is implemented as part of a wearable computing device, and wherein the controller is communicatively coupled to the cardiac sensor through the wearable computing device.

9. The medical device of claim 8, wherein the controller is also part of the wearable computing device.

10. The medical device of claim 9, wherein the wearable computing device is a smart watch.

11. A method for detecting seizures in a patient, comprising:

receiving at a controller, a heart rate of the patient measured by a cardiac sensor over at least a first time period equivalent to three heart beats of the patient, calculating a first slope with the controller, the first slope being at least an estimate of a rate of change in the heart rate over the first time period;

determining, with the controller, a difference between the first slope and a reference slope, the reference slope being a reference value for changes in R-R interval durations during non-ictal conditions;

detecting, with the controller, an epileptic seizure based upon the difference between the first slope and the reference slope; and automatically delivering a warning and a treatment to the patient in response to detecting the epileptic seizure, the treatment being one of an electrical stimulation and a seizure drug treatment;

wherein the first slope is calculated by comparing a time interval between a first R wave peak and a second R wave peak with a time interval between the second R wave peak and a third R wave peak.

12. The method of claim 11, wherein the reference slope is based upon one or more heart rate measurements performed under inter-ictal circumstances including at least one of physical activity, resting, high ambient temperature, daytime, and nighttime.

13. The method of claim 11, further comprising:

receiving, at the controller, at least one autonomic signal in addition to the heart rate;

wherein detecting the epileptic seizure further comprises utilizing the at least one autonomic signal, along with the first slope;

wherein each autonomic signal of the at least one autonomic signal is one of cardiac, vascular, respiratory, and dermal.

14. The method of claim 13, wherein detecting the epileptic seizure further comprises performing a cluster analysis in a state space having a dimension for each of the at least one autonomic signal and a dimension for the first slope, the cluster analysis using a centroid defined, at least in part, by the reference slope.

15. The method of claim 11, wherein the detection of the epileptic seizure occurs in real-time.

16. The method of claim 11, further comprising:

calculating a seizure duration and a seizure intensity;

quantifying the epileptic seizure by calculating a severity of the epileptic seizure;

wherein the severity is a product of the seizure duration and the seizure intensity;

wherein the seizure duration is an amount of time the difference between the first slope and the reference slope spent outside a threshold value; and wherein the seizure intensity is a maximum value of the first slope during the epileptic seizure.

17. The method of claim 16, further comprising classifying, with the controller, the detected epileptic seizure in response to determining that at least one of the seizure intensity and the seizure duration are above a 75th percentile or below a 25th percentile of values for representative seizures.

18. The method of claim 11, wherein the cardiac sensor is part of a wearable computing device, and wherein the controller is communicatively coupled to the cardiac sensor through the wearable computing device.

19. The method of claim 18, wherein the controller is also part of the wearable computing device.

20. The method of claim 19, wherein the wearable computing device is a smart watch.

* * * * *